United States Patent [19]

Pelc et al.

[11] Patent Number: 4,580,219

[45] Date of Patent: Apr. 1, 1986

[54] METHOD FOR REDUCING IMAGE ARTIFACTS DUE TO PROJECTION MEASUREMENT INCONSISTENCIES

[75] Inventors: Norbert J. Pelc, Wauwatosa; Gary H. Glover, Waukesha, both of Wis.

[73] Assignee: General Electric Company, Milwaukee, Wis.

[21] Appl. No.: 490,604

[22] Filed: May 2, 1983

[51] Int. Cl.[4] .............................................. G06F 15/42
[52] U.S. Cl. ...................................... 364/414; 378/4; 378/901; 382/54
[58] Field of Search ............................... 364/413–414, 364/570-572; 378/4, 14, 18-20, 901; 358/111; 382/6, 54

[56] References Cited

U.S. PATENT DOCUMENTS

| | | | |
|---|---|---|---|
| 3,011,057 | 11/1961 | Anger | 250/71.5 |
| 4,068,306 | 1/1978 | Chen et al. | 364/414 |
| 4,070,707 | 1/1978 | Barber | 364/414 |
| 4,075,492 | 2/1978 | Boyd et al. | 250/445 T |
| 4,091,416 | 5/1978 | Riethmuller et al. | 358/111 |
| 4,112,303 | 9/1978 | Brandt | 250/445 T |
| 4,115,695 | 9/1978 | Kelman | 250/445 T |
| 4,115,696 | 9/1978 | Truscott | 250/445 T |
| 4,216,381 | 8/1980 | Lange | 250/363 S |
| 4,217,641 | 8/1980 | Naparstek | 364/414 |
| 4,272,680 | 6/1981 | Cotic | 250/375 |
| 4,272,820 | 6/1981 | Lux | 364/414 |
| 4,275,444 | 6/1981 | Ryan | 364/414 |
| 4,280,178 | 7/1981 | Nassi et al. | 364/414 |
| 4,418,387 | 11/1983 | Yamaguchi et al. | 364/414 |
| 4,433,380 | 2/1984 | Abele et al. | 364/414 |
| 4,463,375 | 7/1984 | Macovski | 358/111 |
| 4,482,958 | 11/1984 | Nakayama et al. | 364/414 |

OTHER PUBLICATIONS

Brooks and DiChiro, "Principles of Computer Assisted Tomography (CAT) in Radiographic and Radioisotopic Imaging", *Phys. Med. Biol.*, vol. 21, No. 5, pp. 689-732, 1976.

Brooks, R. A. et al, "Aliasing: A Source of Streaks in Computed Tomography," *J. Comp. Assist. Tomog.*, vol. 3, pp. 511-518, 1979.

*Primary Examiner*—Gary V. Harkcom
*Attorney, Agent, or Firm*—Alexander M. Gerasimow; Douglas E. Stoner

[57] ABSTRACT

A method is provided for reducing streak artifacts in images reconstructed from projections having significant discrepancies between the first and last scan views due to subject motion or to scan geometry aberrations during a typical 360° scan such as that utilized in computerized tomography. The views taken at the beginning and end of the 360° scan are taken far apart in time, but in the image reconstruction process, they are treated as being adjacent. The method recognizes that in a 360° scan each ray in a projection is scanned twice so that the data set contains redundant information. To reduce the inconsistencies, weights less than the nominal weight are assigned to original projections at the beginning and end of the scan, and the views near the middle of the scan containing corresponding redundant data are compensated so that the combined weights of all ray pairs are constant. In this manner, the inconsistency between the first and last views is feathered out, and the resulting image exhibits significantly reduced sensitivity to errors caused by the discrepancies. The method is effective regardless of the modality (for example, ultrasound, emission nuclear tomography, computerized tomography, nuclear magnetic resonance) used to obtain the projection data.

54 Claims, 16 Drawing Figures

METHOD FOR REDUCING IMAGE ARTIFACTS DUE TO PROJECTION MEASUREMENT INCONSISTENCIES

BACKGROUND OF THE INVENTION

This invention relates to a method for reducing artifacts due to projection measurement inconsistencies at the beginning and end of a scan. More specifically, the invention relates to such method particularly suitable for use with imaging modalities such as, for example, transmission-computed tomography (CT), emission-computed tomography, nuclear magnetic resonance (NMR), and ultrasound.

Each of the aforeidentified imaging modalities may utilize sets of projection data obtained at a plurality of projection angles through a transaxial slice of an object undergoing examination. The projection data are used to reconstruct images of the slice. The preferred embodiments of the invention utilizing divergent ray fan beam and parallel ray beam projections will be disclosed herein with reference to medical diagnostic applications of transmission-computed tomography and emission-computed tomography, respectively. Such images also find uses in many non-destructive testing applications which are contemplated within the scope of the present invention. As used herein, the term "transmission-computed tomography" refers to measurement of radiation transmitted through an object and will also be referred to hereinafter as CT. Emission-computed tomography refers to measurement of radiation emitted from within the object by, for example, radio-pharmaceutical isotopes.

In the simplest of scan geometries, the projections are obtained by measuring the transmission or emission of radiation along parallel ray paths. Early CT apparatus utilized a radiation source collimated to produce a "pencil" beam of radiation with a single detector to detect radiation not absorbed or scattered by the object. A projection was obtained by the joint translation of the source and detector so as to linearly scan the object. The beam, intensity modulated by the internal features of the object intercepting the radiation, was detected and converted to an electrical signal of corresponding intensity. After a first pass across the object, the angle of the beam (hence, that of the projection) was rotated by a small amount relative to the object and the translation repeated. The process was continued so as to obtain projections or views covering at least 180° of an arc. A large number of current readings were made at a large number of points during the linear translate motion.

Emission-computed tomography can also be performed using a translate-rotate technique. Briefly, a single collimated detector would translate and rotate and thereby measure the emission of radiation from the body along sets of parallel rays. It is more common for a scintillation camera equipped with a parallel hole collimator to be used. The collimator defines the parallel rays. The camera is made to rotate about a stationary object. In this way, the translation motion is eliminated and only rotation through the set of angles is necessary to obtain a plurality of projections, as will be more fully disclosed hereinafter.

In more sophisticated systems, such as in most current CT apparatus, the parallel ray beam is replaced by a single fan beam of radiation composed of divergent rays which are detected simultaneously by a plurality of detectors. In one preferred CT scan geometry, the source and detectors are made to orbit jointly about an isocenter to obtain projections for a full 360 degrees. Fan-beam scanning may also be employed in emission-computed tomography and in ultrasound imaging.

In NMR, parallel-ray projections are obtained by varying the directions of magentic-field gradients within a transverse slice of an object to be studied. With each gradient direction corresponding to a projection, the gradient directions are varied to obtain projections from at least 180° of an arc. A detailed exposition of NMR principles may be found in "Nuclear Magnetic Resonance Imaging in Medicine," *Igahu-Shoin*, L. Kaufaman, et al, Editors, and in "NMR Imaging in Biomedicine," *Academic Press*, P. Mansfield and P. G. Morris.

The projection data obtained by any of the aforementioned methods are processed with the aid of a digital-computer means in accordance with techniques well known to the art to produce the desired transverse images. A preferred reconstruction technique employs convolution and back projection of the data. A detailed description of this and other suitable reconstruction techniques is provided by Brooks and Di Chiro in "Principles of Computer-Assisted Tomography (CAT) and Radiographic and Radioisotopic Imaging" *Phys. Med. Biol.*, Volume 21, No. 5, pages 689–732, 1976.

A problem frequently encountered in reconstructing images from projections is that, regardless of the modality used or the particular beam geometry employed to obtain the projection data, a finite period of time elapses between the acquisition of the first projection and the last projection. If, during this interval, the object moves continuously, most projections will be consistent with their neighbors, but the first and last views will be inconsistent. As a result, streak artifacts pointing to the position of the radiation source (in the case of CT) when the first and last projections were measured will appear in the reconstructed image. Even if the object moves abruptly, some inconsistency between the first and last projections may be present, and streaks in the direction of the first/last projection (in addition to other motion artifacts) may be visible. Such artifacts in the reconstructed images may be also due to subtle error in the rotational motion of the scanner or mechanical stability of the device.

A related problem can arise in practical scanning machines used to collect projection data. In CT machines, or example, if the detector and X-ray tube are not rigidly mounted on the rotating member, there may be a gravitationally induced relative motion between them and mechanical hysteresis. This undesired component of hysteresis will cause projection inconsistencies which in turn can produce streak artifacts in the image much like those due to object motion. In NMR machines, a similar effect can be caused by non-linearities in the gradient magnetic fields and imbalance between the orthogonal components.

Therefore, as used herein the meaning of the term "motion" should not be limited to the case of motion of the scanned object alone, but should be broadened to include any relative motion effects which result in ray inconsistencies between the first and last views of the scan.

It is, therefore, an object of the invention to provide a method for reducing the effects of motion-related artifacts in images reconstructed from projections having inconsistencies therein.

It is another object of the invention to provide a method for reducing the effects of motion-related artifacts in the reconstructed image by recognizing that projections measured during a substantially complete rotation contain some redundant information and then using such information to diminish the inconsistency by a suitable means of combining the redundant data.

It is a further object of the invention to provide a method for reducing the effects of motion-related artifacts in images reconstructed from projections which is applicable independently of the modality or beam geometry used to obtain the projections.

SUMMARY OF THE INVENTION

In accordance with the invention, a method is provided for constructing images of an object slice which is useful with a plurality of modalities such as, for example, transmission- and emission-computed tomography, nuclear magnetic resonance and ultrasound. The images are constructed from projection data measurements taken through the slice at a plurality of projection angles in the course of a scan of the object slice. The projection measurements are made up of individual ray measurements. The method includes the step of modifying the relative contributions of projection measurements. The relative contribution of projection measurements in a predetermined angular scan region in at least one of the beginning and end of the scan are reduced, while the relative contributions of projection measurements in a second predetermined angular scan region near the middle of the scan are increased. The measurements in the second predetermined region contain, in the absence of object motion or scanner geometry aberrations, similar information to that measured over the first predetermined region. The increase in relative contribution from the centrally located scan measurements compensates for the reduction in contribution of measurements in the beginning and/or the end of the scan. The projection measurements with reduced and increased contributions together with the remaining unmodified measurements are used to construct an image of the object slice. Artifacts attributable to inconsistencies in projection measurements at the beginning and end of the scan are reduced in the resulting image.

BRIEF DESCRIPTION OF THE DRAWINGS

The features of the invention believed to be novel are set forth with particularity in the appended claims. The invention itself, however, both as to its organization and method of operation, together with further objects and advantages thereof, may best be understood by reference to the following description taken in conjunction with the accompanying drawings in which:

FIG. 13 depicts in flow-chart format an image reconstruction sequence utilized with the fan-beam embodiment of the invention using reflections of projection measurements; and.

DETAILED DESCRIPTION OF THE INVENTION

The problem overcome by the invention and one prior-art solution thereto will now be described with reference to parallel-ray-beam-projection data such as that utilized in the aforedescribed translate/rotate scan geometry of the early transmission CT scanners, multiple-angle reconstruction NMR techniques, ultrasound, or in the parallel-hole-collimator embodiment of the emission-computed tomography apparatus to be described hereinbelow.

Figure 1:
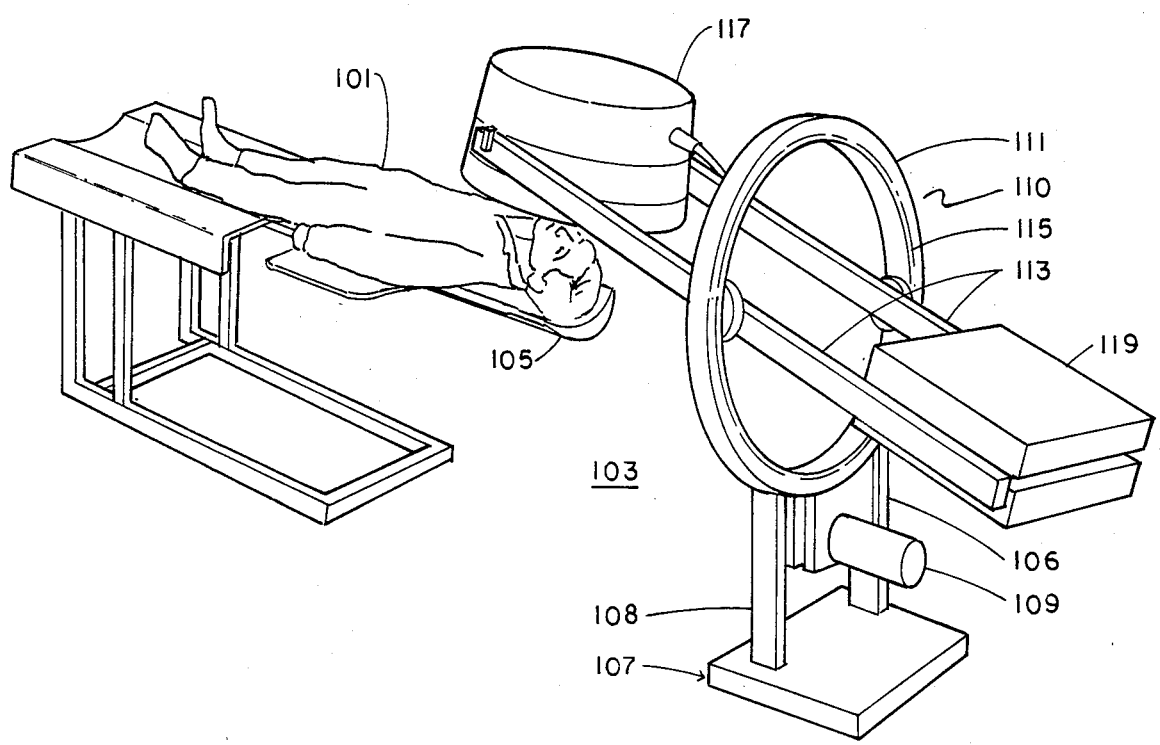
FIG. 1 is a perspective view of an emission-computed tomography apparatus with respect to which one embodiment of the invention is disclosed.

FIG. 1 depicts a patient 101 undergoing examination by an emission tomography camera system 103, while being supported by a cantilevered table 105. As part of this analysis, patient 101 receives an internal dose of radio-pharmaceutical compounds which emit gamma-ray energy. The gamma-ray energy emanating from the patient is detected by a detector 117 for imaging internal portions of the patient. A structure is provided for supporting detector 117 and for rotating the detector in a circular orbit around the patient. The structure includes a base 107 having upright stanchions 106 and 108 extending vertically therefrom and supporting an upright circular frame 110. The upright circular frame comprises an outer circular ring 111 and a concentric inner circular ring 115 adapted for concentric relative rotation. The inner circular ring supports an elongated frame 113. The elongated frame pivotally supports detector head 117 and has a counterweight 119 at the opposite end. Frame 113 is positioned generally at the lateral axis of balance between the detector head and the counterweight so that the detector head can be easily tilted to a desired position. A more detailed description of the emission tomography camera system depicted in FIG. 1 may be found in U.S. Pat. No. 4,216,381, issued to Kai Lange and which is assigned to the same assignee as the present invention.

For emission tomography, patient 101 is generally positioned along the central longitudinal axis of circular frame 110. Detector 117 is carefully positioned so that it is close to the patient and is tangent to the orbital path without interfering with the patient or table. A drive system 109, described in greater detail in aforementioned U.S. Pat. No. 4,216,381, provides the means for rotating elongated frame 113 within circular frame 110 by rotating the inner ring 115 relative to the outer ring 111. The drive system is carefully controlled so that the detector will be advanced in incremental steps while the emission data is being accumulated. As a typical example, the detector is advanced through 128 evenly spaced increments during a 360° orbit of the patient. In theory, a rotation through only 180° would be sufficient, but rotation through 360° is performed to minimize internal attenuation effects insofar as is possible.

Figure 2A:
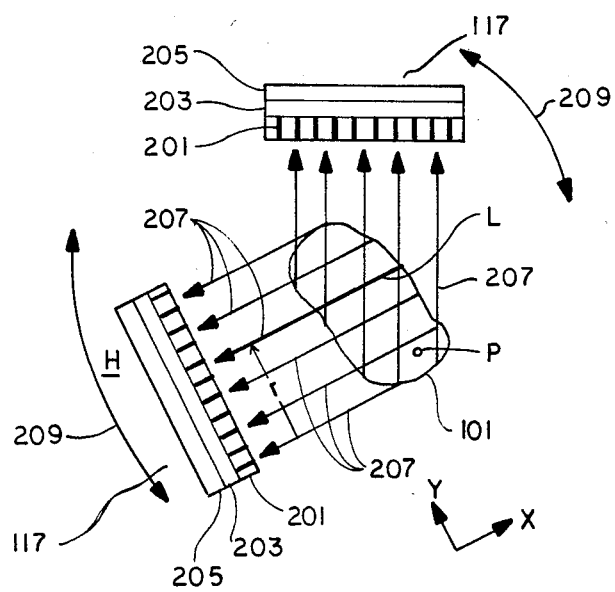
FIGS. 2a and 2b depict schematically the detector utilized with the apparatus of FIG. 1 and with respect to which the parallel-ray-beam-geometry embodiment of the invention is disclosed.

The manner in which the patient is scanned is schematically depicted in FIG. 2a. Detector 117 is illustrated in simplified form as being made up of a parallel hole collimator 201 for admitting gamma rays 207 emitted from patient 101 and travelling along substantially parallel paths toward a scintillator material 203 which generally comprises sodium iodide or cesium iodide. It should be noted that in some emission-tomography apparatus, the collimator is made up of either divergent or convergent holes, such that the projections measured for divergent rays are analogous to the fan-beam-scan geometry utilized, for example, in CT. The fan-beam embodiment of the invention is disclosed hereinafter. Upon excitation by the gamma radiation, the scintillator material emits flashes of light which are converted to electrical currents by photodetectors, such as photomultiplier tubes 205. The induced electrical currents are proportional to the magnitude of the light intensity received. The signals produced by the photodetectors are combined to estimate the location at which the scintillation took place. A detailed description of the operation and structure of a scintillation camera may be found in U.S. Pat. No. 3,011,057. In a typical scan, detector 117 is advanced either clockwise or counterclockwise through a series of positions as indicated by arrows 209 in FIG. 2a to gather information from many directions in a 360° orbit of the patient. The angular position of the detector is encoded to correlate with the emission data. The encoded position on the detector and the signals provided by the scintillation camera are digitized and processed in a well-known manner by means of digital-computer apparatus. This information is then used to reconstruct the gathered data for display in a conventional visual image display device, such as a cathode-ray tube (not shown).

A transmission-computed tomography apparatus such as that schematically depicted in FIG. 9 utilizing a fan-beam geometry will now be described. A body 901 undergoing examination is interposed between an X-ray source 903 and an array of X-ray detectors, generally designated 905, supported in a detector housing 907. In a typical system, the detector housing may, for example, be filled with an ionizable gas, such as xenon, at a high pressure to increase the X-ray-stopping power thereof. X-ray source 903 typically includes a collimation means 909 which functions to confine the X-ray energy emanating from the source to a substantially planar, fan-shaped beam 911. A central sector of X-ray beam 911 irradiates body 901 and is transmitted therethrough to a group 913 of ionization chamber cells in the center of array 905. The angle of the X-ray fan beam is larger than the angle subtended by body 901 so that two peripheral sectors 915 of beam 911 are transmitted past the body without substantial attenuation to two groups of reference cells 917 at the periphery of the array. In a typical array, central group of cells 913 may, for example, comprise as many as 730 separate ionization detector cells, while each of the peripheral detector cell groups 917 may comprise a group of 6 independent cells.

Each cell in the array is made up of a pair of positively charged anode plates 919 and a negatively charged cathode plate 921 interposed therebetween forming an ionization chamber. In operation, X-ray photons entering the ionization chamber interact with the xenon gas and ionize it to produce electron/ion pairs. The positively charged ions are collected at signal electrodes 921 and induce a signal current therein indicative of the X-ray intensity, while the electrons are collected at anodes 919. The electrical signal current obtained at each signal electrode 921 is produced predominantly by X-ray energy entering a single detector cell. In order to obtain X-ray attenuation data from many different angles (needed to reconstruct a CT cross-sectional image), the X-ray source and the detector array are caused, in one embodiment of scan geometries, to rotate jointly either clockwise or counterclockwise about the body, as suggested by arrows A and B in FIG. 9. In a typical CT scan, the X-ray source and the detector array are mounted in a gantry (not shown) and rotated jointly so as to obtain data from 360°. U.S. Pat. Nos. 4,112,303 and 4,115,695 (both assigned to the same assignee as the present invention) disclose details of gantry construction. A preferred embodiment of the detector array is disclosed in U.S. Pat. No. 4,272,680, also assigned to the same assignee as the present invention. It should be noted that the method in accordance with the invention may be advantageously employed with other CT scan geometries such as that, for example, known to those skilled in the art as the "fourth generation." Briefly, in this geometry, the detector comprises a stationary annular structure which surrounds the object to be studied, while the radiation source is caused to orbit the object to obtain measurements from a plurality of projection angles.

Figure 9:
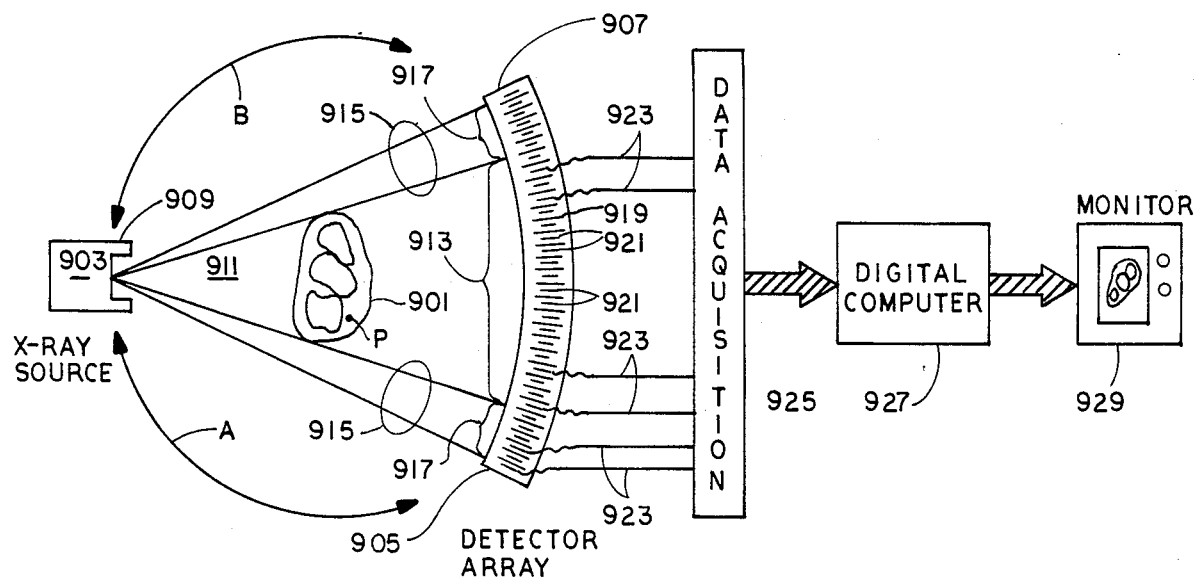
FIG. 9 is a schematic representation of a computerized tomography system with respect to which the fan-beam-scan-geometry embodiment of the present invention is disclosed.

Signals from each detector cell in central group 913 and peripheral group of cells 917 in FIG. 9 are applied by means of data-acquisition channels, such as those generally designated 923 to a data-acquisition means 925 which is of conventional design. From the data-acquisition means, the signals are applied for processing by a digital computer 927 to produce cross-sectional images of body 1 using techniques well known to the art and which will be described in greater detail hereinafter. The reconstructed images may be displayed on a cathode-ray tube monitor 929, for example. The signals provided by the peripheral detector cells 917 in response to excitation by unattenuated radiation from source 903 are utilized to compensate for variations in the intensity of X-ray source 903. Other uses for signals generated by the reference detector cells are disclosed and claimed in U.S. Pat. Nos. 4,068,306 and 4,070,707, both assigned to the same assignee as the present invention.

Figure 2B:
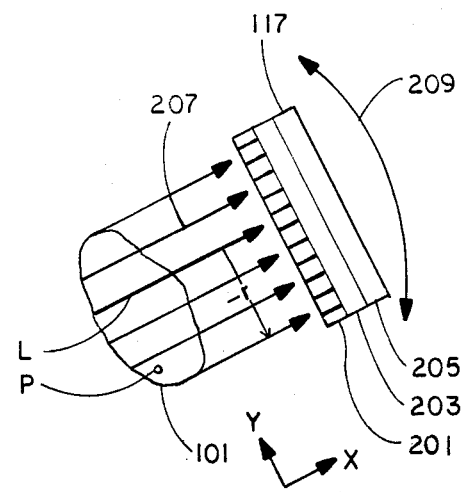
Figure 3:
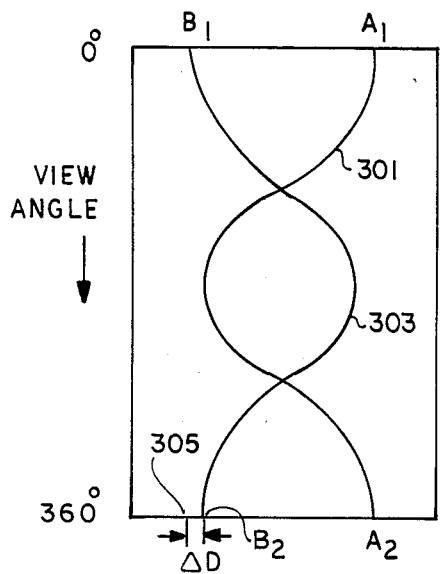
FIG. 3 is a sinogram which depicts graphically the inconsistencies between the first and last views of a scan during which the object undergoing examination has moved.

The data measured during a 360° scan of the object using one of the modalities described hereinbefore can be graphically displayed by means of a sinogram such as that illustrated in FIG. 3. The horizontal axis of the sinogram is the position along a projection, while the vertical axis corresponds to the angles of the measured projections (views). The value at each point in the sinogram is the measured projection value. Consider a single point P within object 101 in FIG. 2a for the parallel-ray geometry used with emission-computed tomography. Because of its particular location, point P will be seen on the right side of the detector at the beginning of the scan process which is indicated in FIG. 2a when the scintillation camera is in position H. As the system rotates clockwise, for example, the point will trace a trajectory on the sinogram as it projects onto points nearer to the center of the detector and eventually onto the left side of the detector (FIG. 2b). At the midpoint of the scan, that is, at 180° from the starting position in a 360° scan, the point will reverse direction and will terminate the trajectory at the starting point. The trajectory traced out is a sine wave for the parallel-beam-scan geometry. The sinusoid is slightly different for points situated in different locations in the object. The amplitude of the sine wave is determined by the distance of a point from the center of rotation while the phase is determined by the angle that the line joining the point with the center of rotation makes when it intersects a reference direction, for example, the X-axis. The radioisotope density (in the nuclear medicine case) determines the amplitude of the measured readings (in the absence of noise) at the point where the point projects onto the detector. For a more complicated object, the sinogram is the superposition of the sine waves for the individual points.

A fan-beam sinogram is a display of the measured projections with the X-axis corresponding to the angle within a fan-beam projection and the vertical axis corresponding again to the angle of the projections. In the fan-beam case, the trajectory of a point is no longer precisely a sine wave but looks very similar to a sinusoid. Since parallel-beam and fan-beam sinograms appear so similar to the eye, both will be described below with reference to FIG. 3.

The sinogram in FIG. 3 shows a trajectory 301 of a point object. The trajectory begins at a position on the detector axis designated $A_1$ and terminates at a point $A_2$ which corresponds to the same point on the axis. For both the parallel- and fan-beam geometries, this coincidence is true only if point P remains stationary during the scan. If point P moves slowly during the scan, then it will start at a point, for example, $B_1$ on the sinogram, but rather than ending at point 305 indicated along the lower horizontal axis in FIG. 3 (i.e., at the same position on the detector axis) it will end at a slightly different point $B_2$. Point $B_2$ is offset from the starting position by a distance $\Delta D$. If the motion of point P during the scan is continuous, most of the projection measurements will be nearly consistent with their neighbors in the central portion of the scan; however, the first and last views will have a discrepancy. Nominally, they should be nearly identical since they measure almost the same projection through the object. In the absence of motion the subtle differences between the first and last views should be similar to the differences between any two adjacent views. Inconsistencies such as those due to motion will manifest themselves in the reconstructed images as streak artifacts that pass through the moving object and point in the direction of the first and last views. Abrupt motion of point P during the scan may also result in discontinuity in the first and last views which will again manifest themselves as streak artifacts in the reconstructed image. Other motion-related artifacts due to projection inconsistencies arising from object motion or geometry aberrations may also be present in the images.

One known method used in transmission-computed tomography, for example, to reduce the effects of inconsistencies between the first and the last views is called overscanning. In this method, data is collected from a scan of the object which exceeds the normal 360° orbit. For example, data may be collected for an additional 40°, that is, between 0° and 400°. This is illustrated on the sinogram depicted in FIG. 4. In the absence of errors, the data taken during the first 40° and for the last 40° of rotation should be redundant (except for measurement noise). In the presence of motion, they will differ and reflect the appearance of the object at the beginning and end of the scan time respectively. In the reconstruction technique utilizing overscan, new views that are weighed averages of the views at the beginning and end of the scan are produced. The weight is made to increase monotonically during the first 40° of the scan and decrease during the last 40° of overscan, as best appreciated by reference to FIGS. 5 and 6.

Figure 4:
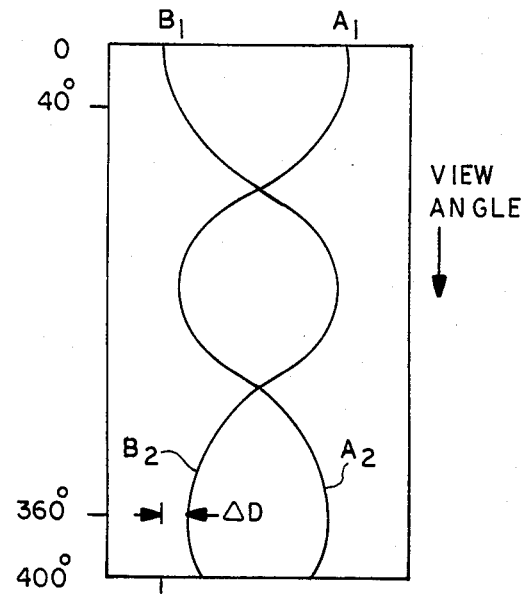
FIG. 4 is a sinogram substantially identical to that of FIG. 3 but which includes overscan data utilized with one prior known method of eliminating artifacts due to object motion during the scan.
Figure 5:
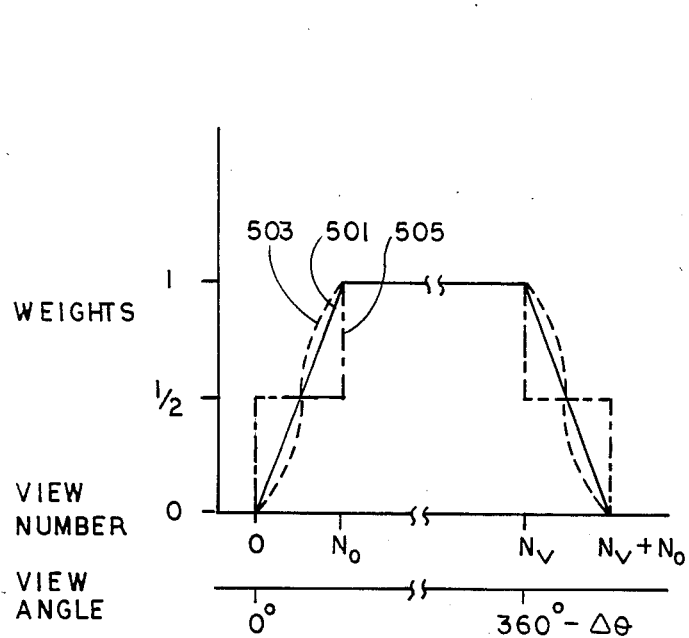
FIG. 5 illustrates graphically several exemplary weight arrangements utilized in the conventional overscan technique to reduce the effects of motion-related data inconsistencies.
Figure 6:
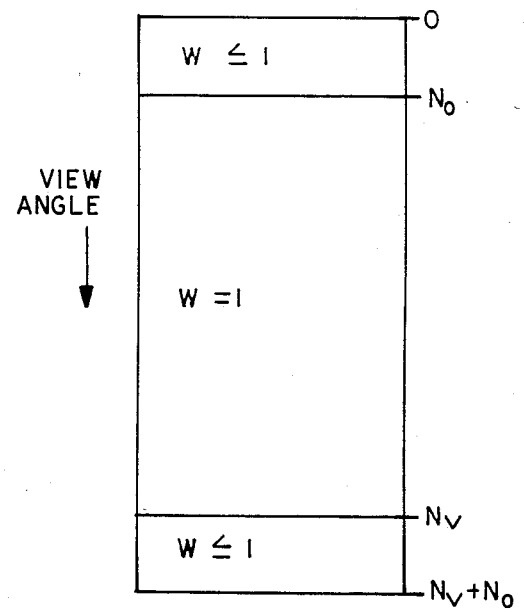
FIG. 6 is a sinogram which depicts the weight distribution for the overscan method of the prior art.

Referring now to FIGS. 5 and 6 and continuing with the description of the conventional overscan method for reducing the effects of motion artifacts, suppose a scan starts with a first view measured at an angle of 0 degrees and $N_v$ projections are measured in a normal scan. The view increment is $\Delta\theta = 360/N_v$ degrees so that the last view in a normal 360° scan would be at $360° - \Delta\theta$, as indicated along the horizontal axis of FIG. 5. Also suppose that a scan is made with $N_o$ views of overscan. In FIG. 4, $N_o$ was arbitrarily selected to correspond to 40°. In the reconstruction, view 1 and view $N_v + 1$ would be combined to produce a new view to replace view 1. In this combination, the old view 1 is weighted very little and view $N_v + 1$ has a much larger weight. The sum of the weight assigned to the views $N_v + 1$ and 1 should be unity as indicated on the vertical axis of FIG. 5. The resulting view is more similar to view $N_v$ (at $360 - \Delta\theta$ degrees) than the original first view. When views 2 and $N_v + 2$ are combined, the weight on view 2 is increased relative to the weight on view 1, while the weight on view $N_v + 2$ is decreased. Again, the sum of the weights of view 2 and view $N_v + 2$ should be unity. This process is continued so that when views $N_o$ and $N_v + N_o$ are combined, the old view, $N_o$, is weighted a lot and the resulting view is similar to view $N_o + 1$ which is not in the overscan region.

The weights may be arranged in any suitable manner, provided the weight pairs for each view add to 1. FIG. 5 illustrates several possibilities. For example, the weights may be linear functions of view angle, as depicted by curve 501, or they may be cubic functions of angle as depicted by curve 503. Combining the weights in accordance with curve 503 is most effective in smoothing out the inconsistencies between the first and last views. Less preferably, the weights may be arranged in a step-wise manner, as indicated by curve 505. The advantage with curve 505 is that the views are essentially averaged, thereby improving the signal-to-noise ratio. Curves 501 and 503 are more effective than curve 505 in reducing motion-related artifacts; however, because the weights are unequal, the signal-to-noise ratio is somewhat lower for curves 501 and 503 than for curve 505. This is not a severe problem, since in all of these the signal-to-noise ratios will be better than that of the conventional non-overscan image. The requirement that the weights for views being combined add to one may be expressed as $W(\theta) + W(360° + \theta) = 1$. The distribution of weights in the overscan sinogram is shown in FIG. 6. Because of the overscan processing, especially if the weights increase and decrease smoothly, any discrepancy due to motion is feathered out and the resulting image will contain fewer artifacts.

From the foregoing, it is apparent that in conventional overscanning, motion-type artifacts are reduced by increasing the amount of rotation in each scan period. In the case where a radiation source is used, such as in transmission-computed tomography, the increase in scan rotation is accompanied by an increase in the radiation dose to the patient. This dose is not delivered uniformly to the patient. It has been shown that this dose, while reducing the image noise somewhat, is not used as efficiently as the dose in a normal scan. Since it is not known before the scan is initiated that motion will occur, this dose and dose-efficiency penalty must be paid for all of the studies where protection from the possibility of motion is desired, whether or not motion actually occurs.

In accordance with the invention, a method is disclosed herein, termed "underscan," which has the ability to reduce motion artifacts utilizing the information in a normal 360° scan. As a result, the dose delivered to the patient is more uniformly distributed. While the application of underscan will cause the quantum noise content of the image to increase somewhat, thus reducing the dose efficiency, this penalty need not be paid all of the time, since the method can be applied retrospectively only when needed. The retrospective application of the method is possible since, in a typical system, the scan data can be electronically stored for later processing. Therefore, in the event that an image exhibits motion artifacts, the underscan method may be used to improve the quality of the image thus, in fact, making the scan more efficient.

The underscan method can be most easily and simply understood with reference to a parallel-beam-scan geometry, such as that described by way of example with reference to FIG. 2a and with additional reference to FIG. 2b for the emission-tomography modality. The underscan method recognizes that the 360° projection measurement data set already contains the required redundant information necessary to compensate for discontinuities between the first and the last views. The views at the beginning and end of the scan still are processed with reduced weights in order to achieve artifact reduction. However, with this method it is not necessary to overscan to obtain the extra views necessary to compensate the reduced weight for the views having inconsistencies. For parallel-ray geometry, as seen in FIG. 2a, a ray L at position r in one projection is duplicated in a position $-r$ in the projection 180° away as seen in FIG. 2b, provided that no motion or geometry errors have occurred during the scan. If motion has occurred, the first view taken at 0 degrees and the last view, $N_v$, will contain inconsistencies which will result in streak artifacts in the direction of these projections. To reduce the impact of the inconsistency on the image, the first view is weighed by a small amount. In an overscan, an extra view was used to compensate for this reduced weight on view 1. However, the 360° parallel-ray data set already contains the required information in view $1 + (N_v/2)$. In underscan, the first view is assigned a weight of $W_1$ and the mirror view, number $1 + N_v/2$, is assigned a weight of $2 - W_1$. Similarly, view $N_v$ receives a reduced weight $W_v$ which can be equal to $W_1$ to maintain symmetry and view $N_v/2$ receives a weight of $2 - W_v$. This technique recognizes that, in a 360° scan, each ray is measured twice, and as long as the combined weights of all pairs is constant, a good image will result.

Figure 7:
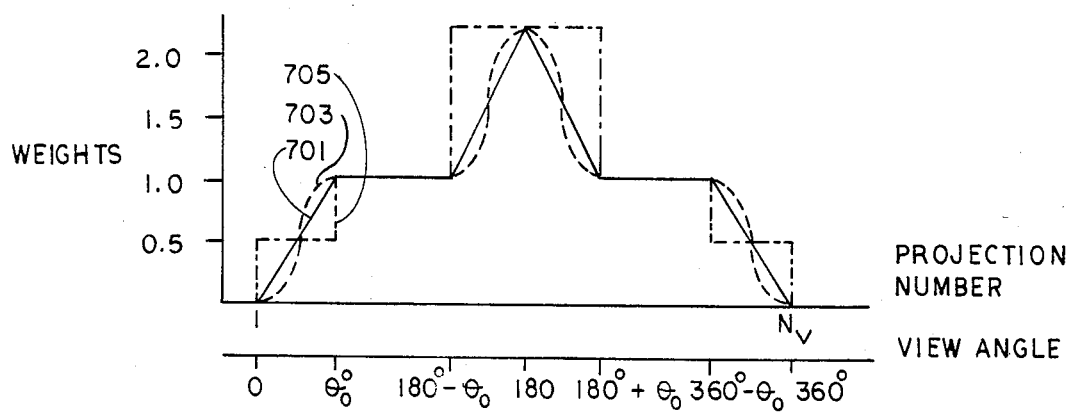
FIG. 7 depicts several exemplary weight distributions utilized with the method of the invention in the parallel-ray-beam-scan geometry to reduce view inconsistencies.
Figure 8:
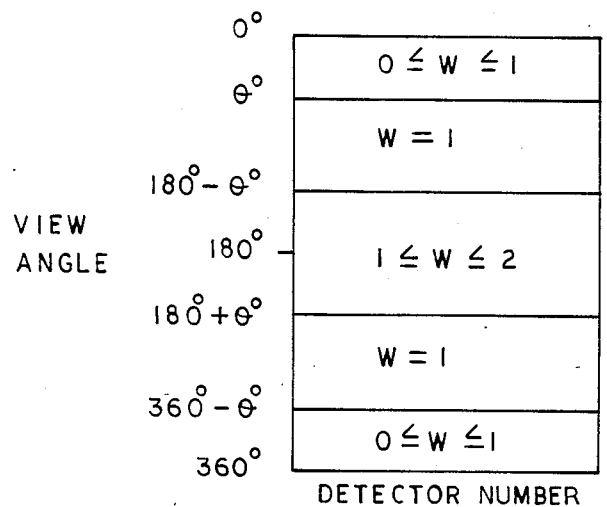
FIG. 8 is a sinogram which depicts the weight arrangements utilized with the method of the invention for the parallel-ray-beam-scan geometry.

The possible manner of arranging the weights is depicted graphically in FIG. 7 and by means of a sinogram in FIG. 8. Referring now to FIG. 7, it will be seen that the weights are typically increased monotonically toward 1 at the beginning of the scan for view angles between 0 and $\theta_o$, as indicated along the horizontal axis. The weights are reduced monotonically at the end of the scan between view angles of $360° - \theta_o$ and $360°$. Compensatory weights are applied to the views near the middle of the data set between view angles $180° - \theta_o$ and $180° + \theta_o$. The compensatory weights applied to views near the middle of the scan data set are needed in order to keep the combined weights of all pairs constant. Because of the reduced weights at the beginning and end, the resulting image will have significantly reduced sensitivity to errors caused by discrepancies between these views. Curves 701, 703, and 705 in FIG. 7 illustrate three exemplary arrangements which may be used for the weights in the underscan technique. Curve 701 is a linear function of view angle. Curve 703 depicts the use of cubic functions of view angle for the regions where the weights are not equal to one and represents the preferred arrangement, since it has the greatest effectiveness of the three in reducing motion-related artifacts. Curve 705 shows the use of piecewise-constant weights and is the least effective of the three in reducing motion artifacts.

In general, it will be recognized that, since a correspondence can be drawn between ray measurements, p, (see FIGS. 2a and 2b) such that $p(r, \theta) = p(-r, 180° + \theta)$, all that is required for the underscan method in a parallel-ray-beam-scan geometry is that the sum of the weight for a ray at $(r, \theta)$ and the weight for a ray at $(-r, 180° + \theta)$ equals a constant. In FIG. 7, the constant was arbitrarily selected to be 2. It will be appreciated that the weights need not be constant across a view. Note also that for the paralel-beam case, if one view is weighted by the same factor for all of the rays in the view, the compensating weights will also be constant over the view 180° away.

Figure 10:
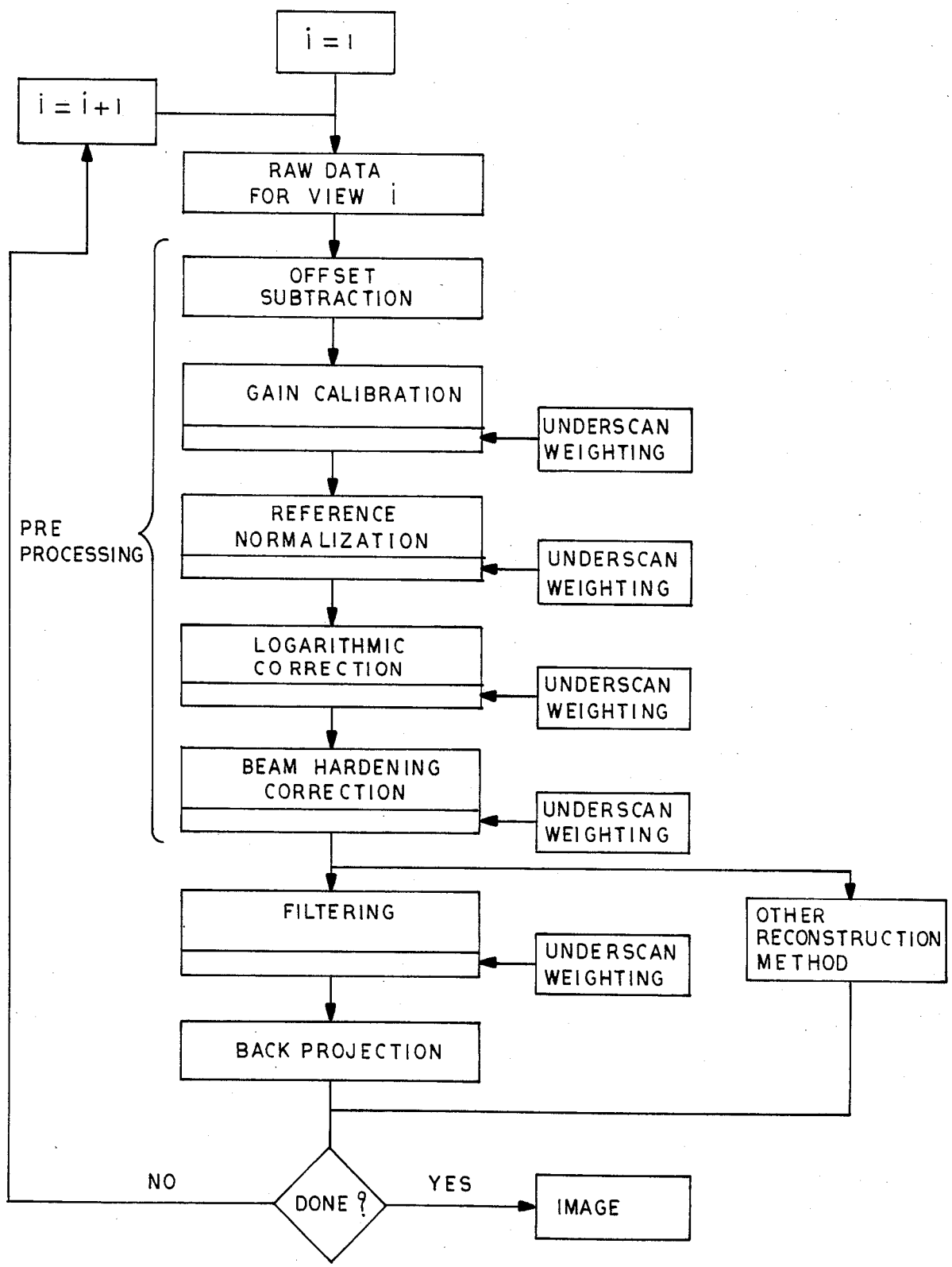
FIG. 10 depicts in flow-chart format a preferred image reconstruction method and indicates various places in the reconstruction sequence where the method of the invention may be advantageously incorporated into the reconstruction process.

FIG. 10 is a simplified summary in flow-chart format of the processing steps in reconstructing an image from either parallel-ray or fan-beam projections. This sequence of steps is well known to those skilled in tomographic imaging. Additionally, FIG. 10 shows that the underscan weighting method in accordance with the present invention can be incorporated into the reconstruction process at preferably one of various positions. Generally, the reconstruction process includes preprocessing of the measured data which is then followed by image reconstruction by one of several available methods. In the preferred embodiment, backprojection of filtered projections is used. Filtering may be accomplished by a number of methods known to the art by, for example, convolution or frequency space filtering using Fourier transformation. However, other reconstruction methods could be used, for example, Fourier reconstruction, backprojection followed by deconvolution, or any of the available iterative methods. Those skilled in the art will recognize that the steps involved in the preprocessing of the data vary from modality to modality and possibly from one system to another.

FIG. 10 shows steps typical of those used for transmission tomography. In this flow chart, i is the view index and reconstruction begins with preprocessing of the first view. Preprocessing begins with the step of offset correction needed to compensate for the fact that even without any X-ray excitation there may be what is called a "dark current" produced in the detectors or electronics. The offset correction step eliminates this current by subtracting it. Gain compensation is necessitated by the fact that each data channel, such as data-transmission channels 923 in FIG. 9, may have different gain due to the unequal sensitivity of the detector cells themselves, or due to the electronic gain variations. Following the gain-correction step is the first point in the reconstruction sequence where the method of the present invention may be employed to adjust the weights assigned to various measurements so as to reduce artifacts caused by inconsistent views at the beginning and at the end of the scan. The reference-normalization step is utilized to compensate for the fact that the X-ray beam intensity during any given view can vary. The normalization is performed by monitoring the X-ray beam intensity by means of one or more of the reference detector cells 917 depicted at the periphery of detector 907 in FIG. 9. Alternatively, the intensity of the X-ray source may be monitored by detectors positioned near collimator 909. The method of the present invention can be inserted after this normalization step. The method may alternatively be applied following the logarithmic-correction step which generally follows the normalization step in the pre-processing sequence of a transmission tomographic scanner. The method may alternatively be applied following the step of beam-hardening correction which follows the step of the logarithmic correction. The beam-hardening correction step is necessitated by the fact that X-ray are not monochromatic so that the lower energy X-rays are preferentially absorbed. The transmitted X-rays are richer in high energies and become more penetrating or "harder" so that a uniform material appears progressively less dense. Such hardening, if uncorrected, may introduce an artifact known as "cupping" in the reconstructed images. If the filtered backprojection method is used, the beam-hardening step is followed by filtering, for example, by convolving the data with the convolution filter. Alternatively, the preprocessed data may be used as input to one of the alternate reconstruction methods. In the case where filtered backprojection is used, the filtered projection is backprojected. If weights that are uniform across projections are chosen, the method of the present invention may be inserted after the filtering step. This entire process is repeated for all views. If iterative reconstruction techniques are used, the various views are processed several times and are compared to calculated views produced from a prior estimate of the object. In this comparison any weighting applied to the data must be taken into account, for example, by comparing the weighted measured projections produced in accordance with the invention to similarly weighted calculated projections.

Figure 11:
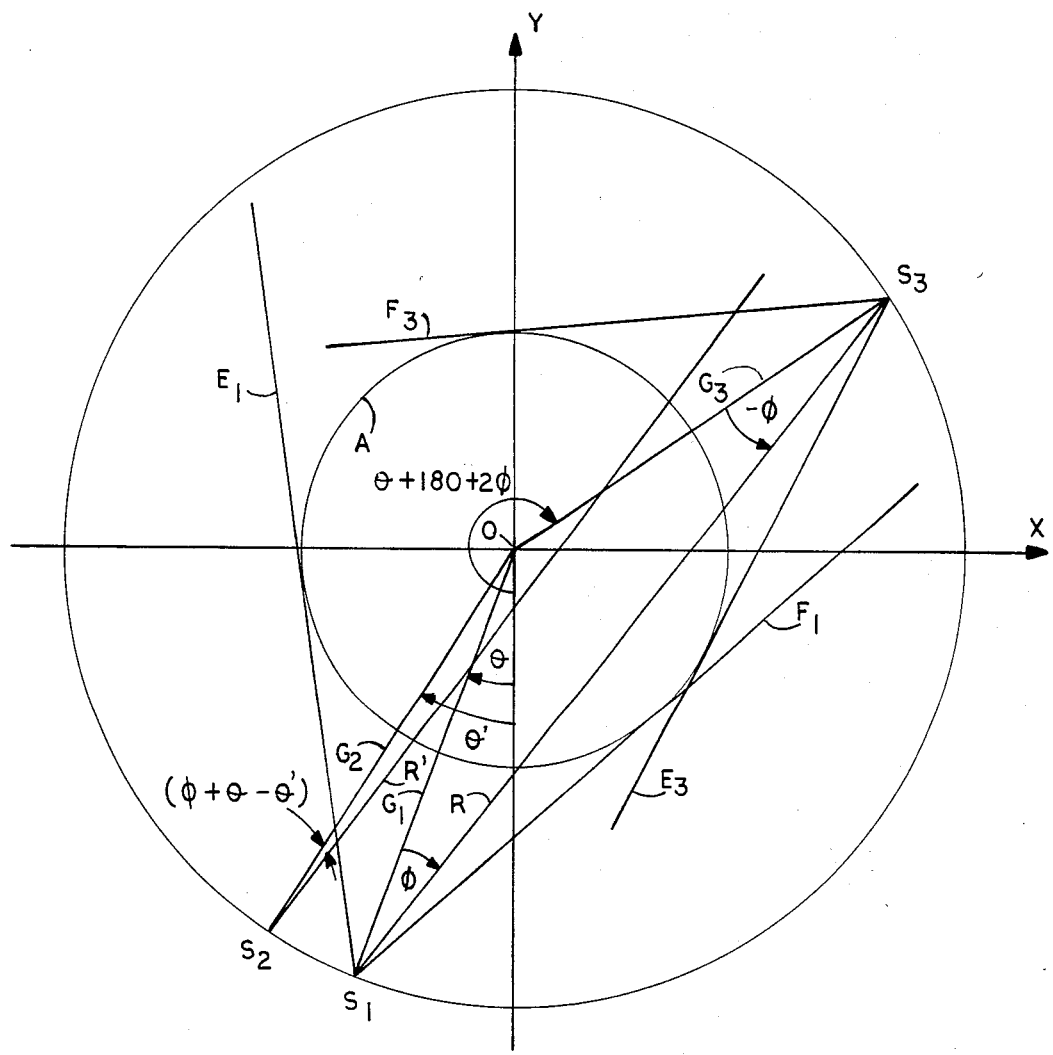
FIG. 11 depicts three exemplary positions of the fan-beam X-ray source and illustrates that the ray that contains equivalent information in a fan-beam-scan geometry may not be in the view measured 180° away.

The application of the underscan method of the invention is slightly more complicated in the fan-beam geometry. Three general embodiments that could be used to reduce motion artifacts in the fan-beam situation will be disclosed. The fan-beam geometry is shown in FIG. 11 which will be described in more detail below. To facilitate the description, some notation is defined first. Let $p(\theta, \phi)$ be the measured projection value for the ray at an angle $\phi$ (FIG. 11) with respect to the central ray of the fan-beam projection measured at an angle $\theta$ with respect to some reference direction, for example, the negative Y axis. A clockwise rotation of the fam beam causes $\theta$ to increase. Similarly, a clockwise excursion within the fan beam is defined to cause an increase in $\phi$.

The first way the present invention can be applied to fan-beam-scan geometry is to use the underscan method with the methods of reordering and rebinning, as described, for example, in U.S. Pat. No. 4,075,492 issued to Boyd et al, which is assigned to the same assignee as the present invention and which is incorporated herein by reference. The methods of reordering and rebinning are used to produce a set of parallel-ray projections from the fan-beam projections. These methods rely on the fact that, while the measurements within a fan-beam projection are not along parallel rays, proper sorting of fan-beam projections can produce sets of measurements along rays that are nearly parallel. In particular, the measurements $p(\theta, \phi)$ and $p(\theta', \phi+\theta-\theta')$ are line integrals made along parallel lines. This may be best appreciated with reference to FIG. 11 in which for one particular view the radiation source is positioned at a point $S_1$. In this view, $G_1$, the central ray of the fan beam, i.e., the ray that passes through the center of rotation 0 which is the origin of the coordinate system, forms an angle $\theta$ with respect to the negative Y-axis. The limits of the fan beam are defined by the rays $E_1$ and $F_1$ which are tangent to the scan field of view A. Let R be a ray of interest within this fan beam. This ray is at an angle $\phi$ with respect to the central ray $G_1$. FIG. 11 shows a second fan beam formed when the source is in position $S_2$. The peripheral rays of the beam at $S_2$ are not shown to preserve clarity in FIG. 11. This second fan beam is at an angle $\theta'$ with respect to the negative Y-axis. Note that ray R' within the second fan beam is parallel to ray R. The angle of R' with respect to the central ray $G_2$ of the fan beam to which it belongs is $(\phi+\theta-\theta')$. One complicating factor in these reordering methods is that the measurements are generally not made continuously but are discrete in both $\theta$ and $\phi$. As a result, interpolation or other approximations are used, as described, for example, in the above-referenced U.S. Pat. No. 4,075,492. Once the fan-beam measurements are reordered into parallel-beam projections, the projection inconsistency reducing underscan method described above with reference to the parallel-ray-beam geometry can be applied.

Just as in the parallel-beam case, when a fan beam is rotated through 360 degrees all rays are measured twice (except for the effect of the discrete nature of the measurement samples). However, in contrast to the parallel-beam case, in the fan-beam geometry the view that contains information essentially equivalent (except for noise and other such errors) to one particular ray in one view is not necessarily contained in the view that is 180 degrees away. In fact, the ray that contains information essentially equivalent to $p(\theta,\phi)$ is in position $-\phi$ within the view at angle $\theta+180+2\phi$ degrees. This can be written:

$$E\{p(\theta,\phi)\} = E\{p(\theta+180+2\phi, -\phi)\} \quad (1)$$

or equivalently:

$$E\{p(\theta,\phi)\} = E\{p(\theta-180-2\phi, -\phi)\}, \quad (2)$$

where E{.} indicates expected value. Expected values are used in Equations 1 and 2 to take into account that noise and other errors may be present.

Returning to FIG. 11 and the ray R of interest, it can be appreciated that the line integral along R is measured twice; once when the source is at $S_1$ where the view angle is $\theta$ degrees and the ray angle is $\phi$ degrees, and again when the source is at $S_3$ where the view angle is $\theta+180+2\phi$ degrees and the ray angle is $-\phi$ degrees. $G_3$ is the central ray of the fan beam produced when the source is at $S_3$ and $E_3$ and $F_3$ are the limits of this fan beam.

This property of the fan-beam geometry can be used to produce artificial fan-beam projections as described, for example, in U.S. Pat. No. 4,280,178, assigned to the same assignee as the present invention and which is incorporated herein by reference. The process is referred to as reflection and is analogous to reordering fan-beam projections into parallel-ray projections except that the output projections are also of the fan-beam type. This method of creating artificial projections can be used with the motion artifact reducing underscan method described above and applied to fan-beam applications. Using reflection the fan-beam projections near the middle of the scan are used to produce new fan-beam projections for the angles near the beginning and the end of the scan. These artificial projections are then combined with the original measured projections to produce yet another set of corrected fan-beam projections. The manner in which the original and artificial projections are combined can be chosen so that the resulting projections produce an image with reduced motion artifacts, as described below.

One possible approach is to generate, using the reflection technique, views for the angular region corresponding to either the beginning or the end of the scan. These artificial views would then be combined with the original views in the manner described above in the discussion of the conventional overscan method. Some artifact reduction would result. However, whereas conventional overscan views are consistent with the views corresponding to the end of a 360° scan, the artificial views may not be consistent with the actual measured views collected at the scan extremes. Thus, this method would not work as well as a conventional overscan.

A somewhat better approach is to use reflection to generate views that correspond in angle with both the beginning and the end of the scan. Let $p(\theta, \phi)$ be the measured fan-beam view at angle $\theta$ and $p_r(\theta, \phi)$ be the artificial view generated using reflection for this angular position. Artificial views can be calculated for the angular range from 0 to $\theta_o$ degrees and from $(360-\theta_o)$ to 360 degrees. Values of between 30 and 60 degrees could be used for $\theta_o$, for example. The original views can be combined with the artificial views by:

$$\hat{p}(\theta,\phi) = W(\theta,\phi) \cdot p(\theta,\phi) + \{1-W(\theta,\phi)\} \cdot p_r(\theta,\phi), \quad (3)$$

where $W(\theta,\phi)$ is the weight applied to the original view at angle $\theta$, and $p(\theta,\phi)$ is the output view resulting from the combination. The image would be reconstructed using these output views in the angular regions for which artificial views are calculated and using the original measured views outside these regions. Note that while in the preferred embodiment the weights are constant along fan-beam projections, the weights could be chosen to not be constant along one fan-beam projection. As was described above, in order to reduce motion artifacts, it is desirable to use reduced weights for the original views near the beginning and the end of the scan.

Figure 12:
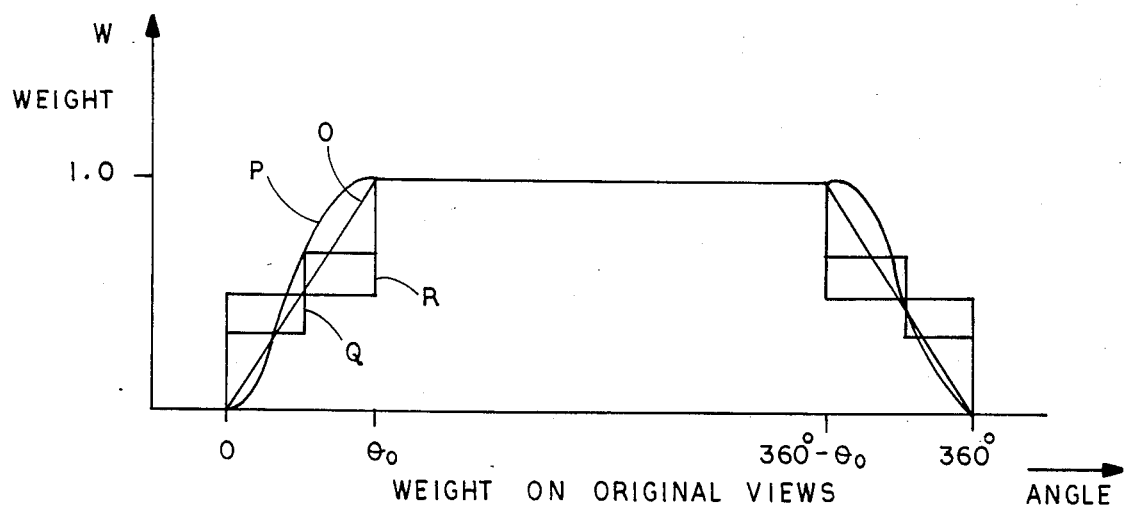
FIGS. 12a and 12b illustrate graphically several exemplary weight arrangements for the original projection measurements and the corresponding weights for artificial views produced in accordance with one embodiment of the invention applied to the fan-beam geometry.
Figure 12:
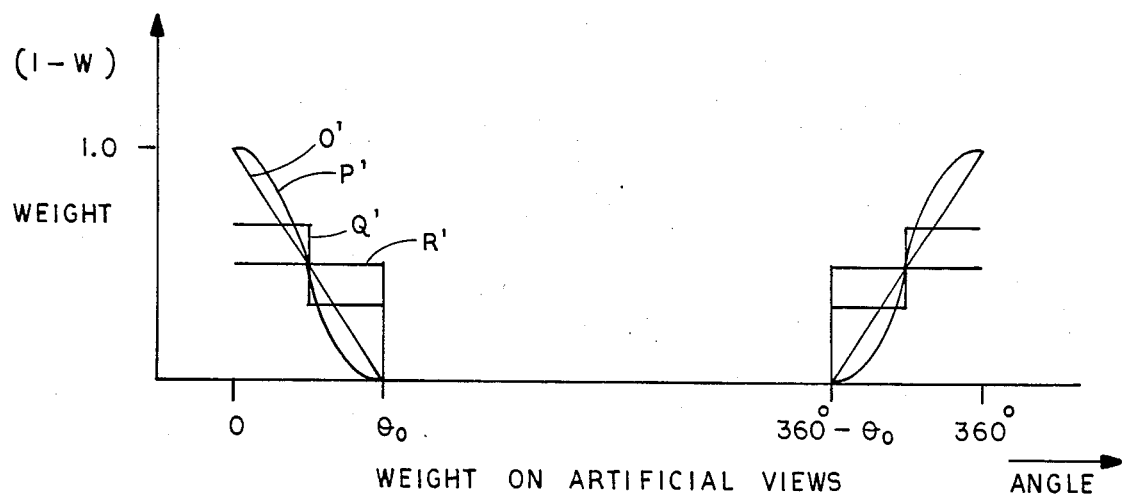

The preferred approach is to use a very small weight for the first original view while the corresponding artificial view receives a much larger weight, and to increase the weight on the original views smoothly until at angle $\theta_o$ the weight on the original view is nearly the nominal weight. The weights on the artificial views would decrease in a similar manner. Weights for the original views that increase with angle in a linear, cubic or some other fashion can be used. The weights would be arranged analogously at the end of the scan. The original view at angle $(360-\theta_o)$ would receive almost the full nominal weight while the artificial view at this angle receives a very small weight. The weights on the original views would decrease with increasing angle while the weights on the artificial views are correspondingly increased until, for the last view angle, the original measured view receives a very small weight while the artificial view receives a much larger weight. This arrangement of weights is shown in FIGS. 12a and 12b which illustrate, respectively, several possible weight distribution configurations for the original views and the corresponding weights for the artificial views. In addition to two arrangements where the weights vary smoothly with angle (curves O, O', P and P', FIGS. 12a and 12b), the use of weights that vary in a step-wise manner is shown (curves Q, Q', R and R', FIGS. 12a and 12b), although they may be less effective in reducing motion artifacts. Note that due to the arrangement of the weights, the effect of inconsistencies between the views at the beginning and end of the scan are reduced by the contribution from the data collected near the middle of the scan (which does not have these inconsistencies). Further, if the weights vary smoothly with angle any inconsistencies between the views in the middle of the scan and those at both the beginning and end are feathered out.

Figure 13:
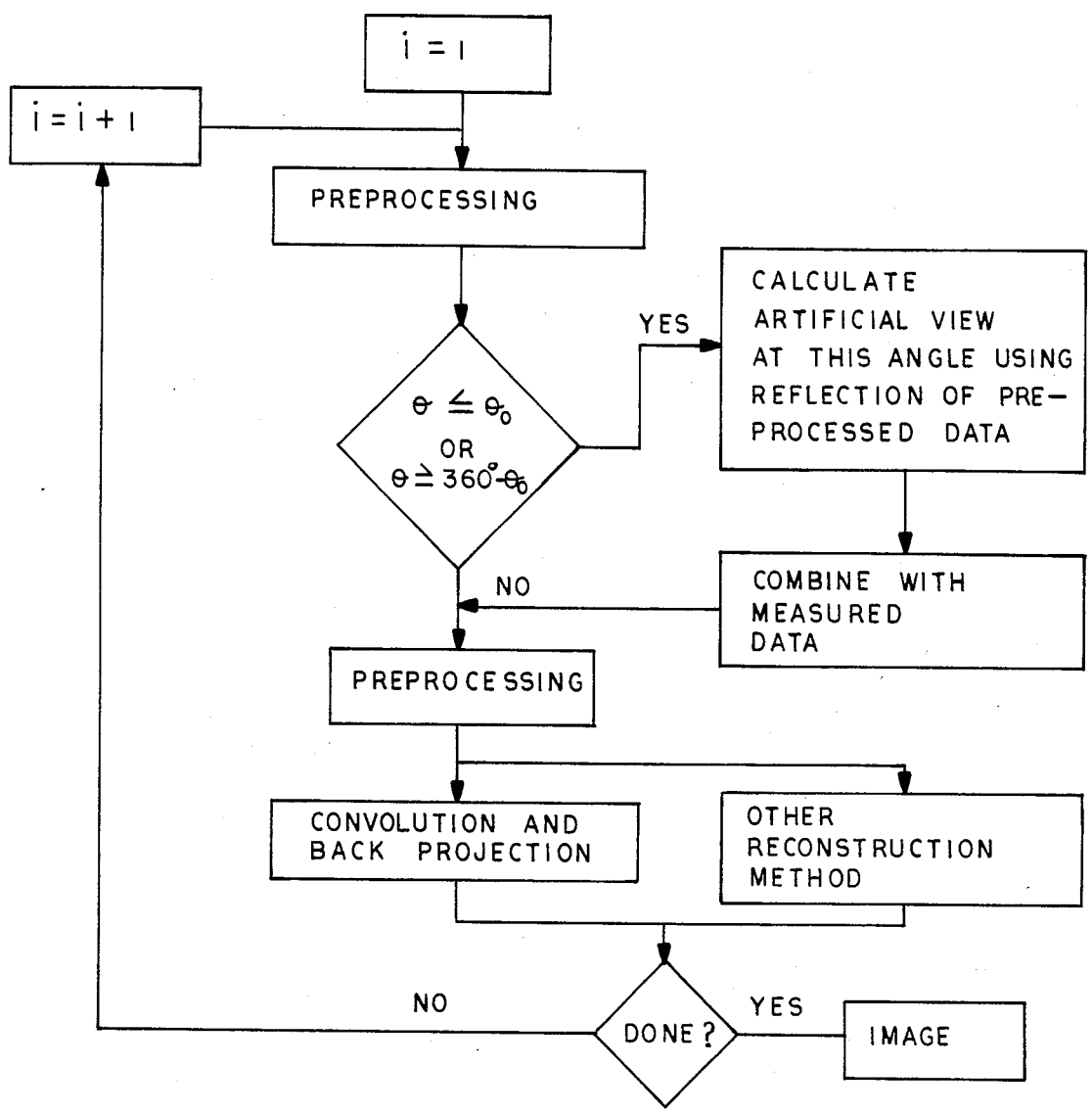

FIG. 13 shows in flow-chart format the major data processing steps involved in the embodiment using reflection. Processing begins with view 1. The projection data is preprocessed as described with reference to FIG. 10. Some or all of the preprocessing steps described in FIG. 10 may be included at this point in FIG. 13. For the view angles within the appropriate regions (e.g., $0°-\theta_o°$) an artificial view is calculated using similarly preprocessed data from the middle of the scan, and the artificial and measured views are combined. The output view, or the measured view for the view angles that are uneffected, is then subjected to any remaining preprocessing steps. Following this, the view is processed in the standard way by the filtered backprojection of other reconstruction algorithm. The process continues until all view angles have been treated.

Both of these approaches for the fan-beam geometry, the use of rebinning and reordering followed by the parallel-beam methods, and the use of reflection to generate artifical fan-beam views to be combined with the original views near the beginning and end of the scan, have some common disadvantages. First, the sorting and reordering required in these methods is time consuming and requires a large amount of memory (not shown) in the digital-computer means. Second and more important, in order to be applied to conventional fan-beam scanners, approximations must be used and these approximations can reduce the spatial resolution of the images. The approximations are due to the fact that conventional scanners do not produce all possible measurements, i.e., measurements for all values of $\theta$ and $\phi$, but instead produce measurements at discrete values of $\theta$ and $\phi$. In general, measurements at the exact locations desired in the sorting process are not available. This problem is usually solved by the use of interpolation or other approximation techniques as described in the aforementioned U.S. Pat. Nos. 4,075,492 and 4,280,178. Since interpolation techniques are not exact, some loss of spatial resolution (sharpness) and accuracy may result.

It will be recognized that the central theme in all of the embodiments of the inventive methods described hereinbefore is to reduce the relative contribution of the measurements made at the beginning and the end of the scan and to compensate for this by increasing the relative contribution of the measurements made near the middle of the scan that contain equivalent information in the absence of motion and other such errors.

In the fan-beam techniques described above, sorting, reordering or rebinning were used essentially to reorganize the available data in such a way that the weighting can be accomplished readily. However, it is possible to derive the way in which the measurements should be weighted directly and to apply this weighting without any reordering.

This method will be described first under the assumption that measurements are available for all $\theta$ and $\phi$. The manner in which discrete cases can be handled will be disclosed hereinafter. Suppose that $p(\theta', \phi')$ is a ray that was measured near the beginning of the scan and it is desired to reduce its contribution in order to reduce the susceptibility to motion artifacts. Suppose that for this reason the weight assigned to ray $p(\theta', \phi')$ i $W(\theta', \phi')$. As was described above, the ray measurement that contains the equivalent inormation about non-moving structures is $p(\theta'+180+2\phi', -\phi')$. This ray must receive a weight of one for its normal position and an additional weight of $\{1-W(\theta', \phi')\}$ to make up for the reduced weight on $p(\theta', \phi')$. Thus:

$$W(\theta'+180+2\phi',-\phi')=2-W(\theta',\phi') \quad (4)$$

Similarly, if $p(\theta', \phi')$ is in the region at the end of the scan, its mirror ray is $p(\theta'-180+2\phi', -\phi)$ and the weight on this mirror is:

$$W(\theta'-180+2\phi',-\phi')=2-W(\theta',\phi'). \quad (5)$$

This can be summarized by stating that for the ray $p(\theta,\phi)$ in the middle of the scan, the proper weight is:

$$W(\theta,\phi)=2-W(\theta-180+2\phi,-\phi) \quad (6)$$

or $$W(\theta,\phi)=2-W(\theta+180+2\phi,-\phi) \quad (7)$$

whichever applies, since $(\theta-180+2\phi)$ and $(\theta+180+2\phi)$ will not both be between 0 and 360 degrees. It may be seen then, that once the weights in the beginning and end of the scan are defined, the compensating weights are given by Equations (6) and (7) above. Note also that, if the weights are constant for fan-beam projections near the beginning and end of the scan, the compensating weights are not constant over fan-beam views. This is due to the fact that the rays that contain information equivalent to that in one fan-beam projection are not all contained in another fan-beam projection.

Figure 14:
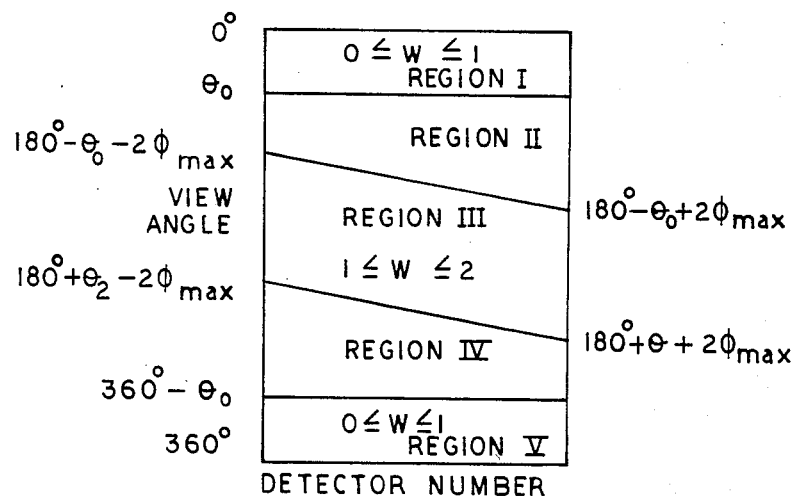
FIG. 14 is a sinogram which illustrates the weight distribution utilized in the method of the invention for views in a fan-beam-scan geometry.

FIG. 14 shows the distribution of weights in a fan-beam sinogram. It can be seen that the weights are less than the nominal weight for the views between 0 and $\theta_o$ degrees (region I), are equal to the nominal weight for a while (region II), are higher than the nominal weight in a diagonal swath of the sinogram (region III), are again equal to the nominal weight in region IV, and are lower than the nominal weight at the end of the scan (region V). Note that the allowed values of $\theta_o$ are limited by the fact that if $\theta_o$ is too large regions I and III will overlap. In particular, $\theta_o$ must satisfy $$\theta_o \leq 90 - \phi_{max} \quad (8)$$

where $\phi_{max}$ degrees is the largest divergence of the fan beam from the central ray (i.e., $\phi_{max}$ is equal to one half of the full fan angle).

The arrangement of weights may be better understood by examining one particular case in more detail, for example, the use of weights that increase as cubic functions of angle and are constant over fan-beam views at the beginning of the scan. Assume that it is desired to have the weights be zero for the view measured at 0 degrees, have zero slope at this angle, and increase to a value of one at an angle of $\theta_o$ where they again have zero slope. This is given by:

$$W(\theta,\phi)=3(\theta/\theta_o)^2-2(\theta/\theta_o)^3 \text{ for } 0\leq\theta\leq\theta_o \quad (9)$$

Suppose that a similar arrangement of weights is desired for the views at the end of the scan, at angles ranging from $(360°-\theta_o)$ to 360 degrees. This is given by:

$$W(\theta, \phi) = 3\left(\frac{360-\theta}{\theta_o}\right)^2 - 2\left(\frac{360-\theta}{\theta_o}\right)^3 \text{ for } (360-\theta_o) \leq \theta \leq 360 \quad (10)$$

To compensate for these reduced weights, the weights in the middle of the scan are:

$$W(\theta, \phi) = \begin{cases} 2 - 3x^2 + 2x^3 & \text{for } 0 \leq x \leq 1 \\ 1 & \text{otherwise} \end{cases} \quad (11)$$

where $$x = \left|\frac{\theta - 180 + 2\phi}{\theta_o}\right| \quad (12)$$

and $|.|$ indicates absolute value.

If direct fan-beam convolution backprojection is the reconstruction method used, this method of weighting fan-beam projections without reordering is only an approximation since in fan-beam reconstruction the contributions from opposed rays is slightly different.

This difference, however, is very subtle and has been found to cause an error whose magnitude is acceptably small for many applications.

As was described hereinbefore, conventional fan-beam tomographic devices do not collect measurements at all values of $\theta$ and $\phi$, but instead acquire a finite number of samples within each of a finite number of fan-beam projections. Let $p(\theta_i, \phi_j)$ be the j-th sample within the i-th projection. In these discrete cases, rays that exactly superimpose are not available in general. That is, the measurement that is equivalent to $p(\theta_i, \phi_j)$ is $p(\theta_i+180+2\phi_j,-\phi_j)$. In general, a fan-beam projection precisely $(\theta_i+180+2\phi_j)$ degrees will not be available. Further, many fan-beam devices align their samples within each fan beam asymmetrically about the central ray since this reduces certain artifacts (see Brooks, R. A., Glover, G. H., Talbert, A. J., et al; "Aliasing: A Source of Streaks in Computed Tomography" *J. Comput. Assist. Tomog.*, Vol. 3, pp. 511-518, 1979). For example, the center of rotation may project onto a point one quarter of a sample spacing away from the nearest sample. In these cases a sample will not be available at $-\phi_j$ in any view. The most straight-forward way to deal with this situation is to treat the distribution of weights as a continuous functon, as derived, and to use for each of the discrete measurements the value of the continuous weight function at the appropriate angles. Thus, $p(\theta_i, \phi_j)$ would receive a weight of $W(\theta_i, \phi_j)$ where W was calculated for the continuous case.

Again, this may be best understood by examining a particular example. The assumption will be made that $N_v$ fan-beam projections uniformly spaced over 360 degrees have been acquired. The i-th projection is assumed to have been measured at an angle of:

$$\theta_i = (i-0.5)\cdot\Delta\theta \tag{13}$$

degrees, where $\Delta\theta = (360/N_v)$ degrees is the view increment. (Note that the sign of $\Delta\theta$ should change when the direction of rotation is reversed. In the present example a clockwise rotation is assumed so $\Delta\theta$ is positive.) The range of angles over which the weights on the views at the beginning of the scan will receive progressively increasing weights is specified by choosing it to be a certain number of views, say $N_u$. Thus:

$$\theta_o = N_u \cdot \Delta\theta \tag{14}$$

is the angular range over which weights increase at the beginning of the scan. Continuing with the example of the use of cubic weights, it may be seen that for view indices between 1 and $N_u$ and for view indices between $(N_v-N_u+1)$ and $N_v$ the weights are:

$$W(\theta_i,\phi_j) = 3x^2 - 2x^3 \tag{15}$$

where:

$$x = \begin{cases} \dfrac{i-0.5}{N_u} & \text{for } 1 \leq i \leq N_u \\ \dfrac{N_v-i+0.5}{N_u} & \text{for } (N_v-N_u+1) \leq i \leq N_v \end{cases} \tag{16}$$

For views outside this region, i.e., $(N_u+1) < i < (N_v-N_u)$, the weights are:

$$W(\theta_i,\phi_j) = \begin{cases} 2 - 3x^2 + x^3 & \text{for } 0 \leq x \leq 1 \\ 1 & \text{otherwise} \end{cases} \tag{17}$$

where x is given by:

$$x = \left| \frac{i - 0.5 - (N_v/2) + (2\phi_j/\Delta\theta)}{N_u} \right| \tag{18}$$

Typically, the samples within a fan-beam projection are equally spaced in angle, each sample at an angle $\Delta\phi$ from each of its neighbors. In these cases, $\phi_j$ may be written:

$$\phi_j = (j-c)\Delta\phi \tag{19}$$

where c is the index, including any fractional part, corresponding to the point in the fan beam onto which the central ray projects. Combining Equations (18) and (19) yields:

$$x = \left| \frac{i - 0.5 - (N_v/2) + 2(j-c)\dfrac{\Delta\phi}{\Delta\theta}}{N_u} \right| \tag{20}$$

Note that when the fan beam is aligned substantially symmetrically, i.e., $C \approx (N_d/2)$ where $N_d$ is the total number of samples within each projection, the views in the middle of the scan with samples that receive increased weighting are limited to those whose index is between $\{(N_v/2)-K\}$ and $\{N_v/2+K\}$ where K is:

$$K = N_u + N_d|\Delta\phi/\Delta\theta| + 1. \tag{21}$$

Note again that the weights for the views in the middle of the scan are not constant across a view (Equations (17) and (18). The time required to compute these weights can be reduced by first calculating the weights exactly for view $N_v/2$ and then using interpolation methods to estimate the weights for the other views. Linear interpolation has been found to be adequate for one application.

The flow chart on FIG. 10 applies equally well for fan-beam application as for the parallel-beam case. The only difference is that the weighting process in accordance with the invention in the fan-beam case is best implemented before the filtering step. The weighting process for fan-beam applications can be summarized (for the present example of cubic weights and equally spaced samples within a substantially symmetric fan beam) by the following sequence of steps:

1. Select $N_u$, the number of views during which the weights increase:

$N_u$ corresponding to 60 degrees has been found to be optimal in one situation.

2. Calculate the weight profile for view $N_v/2$ $$W(j) = \begin{cases} 2 - 3x^2 + 2x^3 & \text{for } 0 \leq x \leq 1 \\ 1 & \text{Otherwise} \end{cases} \tag{22}$$

$$x = \frac{-0.5 + 2(j-c)\dfrac{\Delta\phi}{\Delta\theta}}{N_u}, \tag{23}$$

-continued $$C - \left|\frac{\Delta\theta}{2\Delta\phi}\right|(N_u - 0.5) \leq j \leq C + \left|\frac{\Delta\theta}{2\Delta\phi}\right|(N_u + 0.5)$$

3. For the region of increasing weights, $1 \leq i \leq N_u$, weight the entire view by $$W(\theta_i,\phi_j) = 2x^3 - 3x^2 \quad (24)$$

where $$x = i - 0.5/N_u \quad (25)$$

4. For the ramp-down $N_v - N_u + 1 \leq i \leq N_v$, weight the entire view using Equation (8) but with $$x = \frac{N_v - i + 0.5}{N_u} \quad (26)$$

5. For views between $N_v/2 - K$ and $N_v/2 + K$ (K given by Equation (21) calculate t, the amount by which the weight for detector 1 in this view is shifted from its position in W' (Equation (22)

$$t = -\left[\left(i - \frac{N_v}{2}\right)\right]\frac{\Delta\theta}{2\Delta\phi}, \quad (27)$$

The location of the sample in W' to the left of the one necessary for detector 1 is given by:

$$k = CEIL(t) - 1 \quad (28)$$

where CEIL(t) is the lowest integer greater than or equal to t. The linear interpolation weights are:

$$g_2 = t - k \quad (29)$$

and $$g_1 = 1 - g_2 \quad (30)$$

and the weight for the i-th view is:

$$W(\theta_i,\phi_j) = \begin{cases} g_1 W'(j+k-1) + g_2 W'(j+k), & C - \left|\frac{\Delta\theta}{2\Delta\phi}\right|(N_u - 0.5) \leq i \leq C + \left|\frac{\Delta\theta}{2\Delta\phi}\right|(N_u + 0.5) \\ 1 & \text{otherwise} \end{cases} \quad (31)$$

6. All $N_v$ views, including the modified and unmodified ones, are filtered and backprojected, as described briefly with reference to FIG. 10.

In the above description, weights that are uniform across the fan-beam projections at the beginning and end of the scan were used. This property is ideal for uniform suppression of artifacts. However, other weights could be used. For example, constant weights may be used for rays that are substantially parallel. That is, the weight applied to a ray depends on the absolute angle of the ray to a different direction. This is equivalent to rebinning into parallel rays, weighing the parallel data set, and rebinning back to fan-beam projections. In this case, the weights are never constant along fan-beam projection. It should be understood that other weights can also be chosen. The common property is that, to reduce motion artifacts, the weights must be less than 1 for the views near the beginning and end of the scan.

From the foregoing, it will be appreciated that in accordance with the invention a method is provided for reducing the effects of motion-related or scanner-geometry-aberrration-related artifacts in images reconstructed from projections having inconsistencies between the first and last views, due to the fact that the object was moved during the scan interval or the scanner has not perfectly executed its motion. The method is effective in reducing such artifacts independent of the modality used to obtain the projections. For example, the method is applicable to projections obtained in emission-nuclear tomography, computerized tomography, ultrasound, and nuclear magnetic resonance studies. Unlike prior-art methods, the technique in accordance with the invention is effective in reducing motion artifacts by utilizing information contained in normal 360° scans of the object.

In fact, it is possible to use this method to produce an image when the scan covers somewhat less than 360°. Consider, for example, a scan that covers 330 degrees, say from 15 degrees to 345 degrees, and compare it to a full 360-degree scan. Suppose that the full scan had been procesed using the above-described method where, in particular, the views from 0° to 15° and the views from 345° to 360° received zero weight and where the weights for the views near the middle of the scan compensated for this. Now, apply these weights to the 330-degree scan. Since the missing views would receive no wieght, they will not be missed. Thus, increased weights near the middle of the scan can be used to compensate for a scan that does not cover a full 360 degrees. On the other hand, the angular coverage of the scan must be large enough to support regions of nominal, less than nominal, and greater than nominal contribution.

While this invention has been described with reference to particular embodiments and examples, other modifications and variations will occur to those skilled in the art in view of the above teachings. Accordingly, it should be understood that within the scope of the appended claims the invention may be practiced otherwise than is specifically described.

The invention claimed is:

1. A method of constructing images of an object slice which is useful with a plurality of modalities, said images being constructed from projection data measurements taken through the slice at a plurality of projection angles in the course of a scan of said object slice, said projection measurements being made up of individual ray measurements, said method being effective to reduce image artifacts due to inconsistencies in projection measurements in the beginning and end of said scan, wherein said method comprises the steps of:

(a) reducing the relative contribution of projection measurements in a first predetermined angular scan region extending over at least one of the beginning and end of said scan;

(b) increasing the relative contribution of projection measurements in a second predetermined angular scan region near the middle of said scan, which measurements, in the absence of motion, contain similar information to that measured over said first predetermined angular scan region, said increase in relative contribution compensating for said reduced contribution assigned to projection measurements in step (a); and (c) constructing an image using said measurements in said first and second predetermined regions having modified contributions, and also using any remaining unmodified measurements which have not had their contributions reduced or increased, said image having reduced artifacts due to reduced contributions from said projection measurement inconsistencies.

2. The method of claim 1 wherein said first and second predetermined angular scan regions each comprise up to at least a 60° portion of said scan.

3. The method of claim 1 wherein the respective sums of ray measurements in a projection having reduced contributions and the corresponding ray measurements in said second predetermined region containing measurement information similar thereto and having increased contributions are constant.

4. The method of claim 1 wherein said ray measurements comprising said scan are organized into parallel-ray projections.

5. The method of claim 4 where, in the course of a single scan of said object slice, projection measurements are taken over a scan region substantially greater than 180°, but not exceeding 360°.

6. The method of claim 4 wherein said step of reducing comprises assigning weights to projection measurements, wherein said weights increase monotonically as a function of time over said first predetermined angular scan region in the beginning of said scan.

7. The method of claim 4 wherein said step of reducing comprises assigning weights to projection measurements, wherein said weights decrease monotonically as a function of time over said first predetermined angular scan region at the end of said scan.

8. The method of claim 6 or 7 wherein said relative contributions are selected to vary as cubic functions of projection angle over portions of said predetermined regions.

9. The method of claim 6 or 7 wherein said relative contributions are selected to vary as linear functions of projection angle over portions of said predetermined regions.

10. The method of claim 6 or 7 wherein said relative contributions are selected to vary as piecewise-constant functions of projection angle over portions of said predetermined regions.

11. The method of claim 4 wherein the relative contributions of said ray measurements over said first predetermined angular region in a single projection are reduced by a constant amount, and wherein the relative contributions of corresponding ray measurements in a projection measured 180° away in said second predetermined angular scan region are each increased by a constant amount.

12. The method of claim 11 wherein the sums of the relative contributions of the individual ray pair measurements in said first and second predetermined angular scan region which are situated 180° apart relative to one another are all equal to a constant.

13. The method of claim 4 wherein said modality comprises transmission-computed tomography and wherein said step of constructing includes the step of preprocessing all of said projection measurements, said step of preprocessing further including at least one of the steps of gain calibration, reference normalization, logarithmic correction, and beam-hardening correction, said steps of reducing and increasing relative contributions being applied following at least one of said steps of preprocessing.

14. The method of claim 4 or 13 wherein said step of constructing includes the steps of filtering and then backprojecting said projection measurements including said projection measurements having reduced and increased contributions.

15. The method of claim 14 wherein said steps of reducing and increasing relative contributions follow said step of filtering and precede said step of backprojecting.

16. The method of claim 1 wherein said ray measurements comprising said scan are organized into diverging fan-beam projections.

17. The method of claim 16 where, in the course of a single scan of said object slice, projection measurements are taken over a scan region substantially greater than 180°, but not exceeding 360°.

18. The method of claim 16 including at least one of the steps of reordering and rebinning so as to convert said projection measurements organized into divergent rays into projection measurements organized into parallel rays.

19. The method of claim 18 wherein said step of reducing comprises assigning weights to said converted projection measurements, wherein said weights increase monotonically as a function of time over said first predetermined angular scan region in the beginning of said scan.

20. The method of claim 18 wherein said step of reducing comprises assigning weights to said converted projection measurements, wherein said weights decrease monotonically as a function of time over said first predetermined angular scan region at the end of said scan.

21. The method of claim 19 or 20 wherein said relative contributions are selected to vary as cubic functions of projection angle over portions of said predetermined regions.

22. The method of claim 19 or 20 wherein said relative contributions are selected to vary as linear functions of projection angle over portions of said predetermined regions.

23. The method of claim 19 or 20 wherein said relative contributions are selected to vary as piecewise-constant functions of projection angle over portions of said predetermined regions.

24. The method of claim 18 wherein the relative contributions of said ray measurements over said first predetermined angular region in a single projection are reduced by a constant amount, and wherein the relative contributions of corresponding ray measurements in a projection measured 180° away in said second predetermined angular scan region are each increased by a constant amount.

25. The method of claim 24 wherein the sums of the relative contributions of the individual reordered and rebinned ray pair measurements in said first and second predetermined angular scan region which are situated 180° apart relative to one another are all equal to a constant.

26. The method of claim 18 wherein said modality comprises transmission-computed tomography and wherein said step of constructing includes the step of preprocessing all of said projection measurements, said step of preprocessing further including at least one of the steps of gain calibration, reference normalization, logarithmic correction, and beam-hardening correction, said steps of reducing and increasing relative contributions being applied following at least one of said steps of preprocessing.

27. The method of claim 18 or 26 wherein said step of constructing includes the steps of filtering and then backprojecting said projection measurements including said projection measurements having reduced and increased contributions.

28. The method of claim 26 wherein said steps of reducing and increasing relative contributions follow said step of filtering and precede said step of backprojecting.

29. The method of claim 16 further comprising the step of producing artificial fan-beam projection measurements to compensate for inconsistencies present in projection measurements in at least one of the beginning and end of said scan.

30. The method of claim 29 wherein said step of producing artificial projections comprises the steps of
producing a new set of fan-beam projection measurements for said first predetermined region using reflections of corresponding fan-beam projections situated in said second predetermined region; and
combining said new fan-beam projections with existing fan-beam projections for said first predetermined region to produce a set of compensated fan-beam projections, which projections are then used to construct an image having reduced motion artifacts.

31. The method of claim 30 wherein said first predetermined region is selected to be one of the beginning and the end of said scan.

32. The method of claim 30 wherein said first predetermined region is selected to include projection measurements at the beginning and end of said scan, and wherein artificial projections are produced for each of beginning and end of said scan.

33. The method of one of claims 30, 31, or 32 wherein in said step of combining said new fan-beam projections with said existing fan-beam projections the relative contributions of each are selected as monotonic functions of time over said first predetermined region.

34. The method of claim 33 wherein the relative contributions of said new projections and said existing fan-beam projections are selected as cubic functions of projection angle over portions of said predetermined regions.

35. The method of claim 33 wherein the relative contributions of said new projections and said existing fan-beam projections are selected as linear functions of projection angle over portions of said predetermined regions.

36. The method of claim 33 wherein the relative contributions of said new projections and said existing fan-beam projections are selected as piecewise-constant functions of projection angle over portions of said predetermined regions.

37. The method of claim 30 where in said step of combining said new fan-beam projections with said existing fan-beam projections the relative contributions thereof are selected such that the sum of respective pairs thereof is constant for ray measurements within each projection.

38. The method of claim 30 where in said step of combining said new fan-beam projections with said existing fan-beam projections the relative contributions thereof are selected such that the sum of respective pairs thereof varies for ray measurement within each projection.

39. The method of claim 29 wherein said modality comprises transmission-computed tomography and wherein said step of constructing includes the step of preprocessing all of said projection measurements, including said set of compensated projection measurements, said step of preprocessing further including at least one of gain calibration, reference normalization, logarithmic correction, and beam-hardening correction, said steps of reducing and increasing relative contributions being applied following at least one of said steps of preprocessing.

40. The method of claim 29 or 39 wherein said step of constructing includes the steps of filtering and then backprojecting said projection measurements including said projection measurements having reduced and increased contributions.

41. The method of claim 40 wherein said steps of reducing and increasing relative contributions follow said step of filtering and precede said step of backprojecting.

42. The method of claim 40 wherein said steps of reducing and increasing relative contributions follow said step of filtering and precede said step of backprojecting.

43. The method of claim 16 wherein said steps of reducing and increasing relative contributions, and constructing an image are performed without any of the steps of reordering, rebinning and reflecting said projection measurements.

44. The method of claim 43 wherein said steps of reducing and increasing the relative contributions comprises weighting said projection measurements in said first and second predetermined regions with a weighting factor which is a function of the projection angle.

45. The method of claim 44 wherein said weights are selected to be constant for divergent ray measurements within each projection within said first predetermined region.

46. The method of claim 44 wherein said weights are selected to be variable for divergent ray measurements within each projection within said first predetermined region.

47. The method of claim 44 wherein said weighting factors are selected to be lower in said first predetermined region, and higher in said second predetermined regions relative to one another.

48. The method of claim 44 wherein said weighting factors are selected to increase monotonically as functions of time over said first predetermined region at the beginning of said scan.

49. The method of claim 44 wherein said weighting factors are selected to decrease as monotonic functions of time over said first predetermined region at the end of said scan.

50. The method of claim 48 or 49 wherein said weights are selected to be cubic functions of projection angle over portions of said predetermined regions.

51. The method of claim 48 or 49 wherein said weights are selected to be linear functions of projection angle over portions of said predetermined regions.

52. The method of claim 48 or 49 wherein said weights are selected to be piecewise-constant functions of projection angle over portions of said predetermined regions.

53. The method of claim 43 wherein said modality comprises one of transmission-computed tomography and wherein said step of constructing includes the step of preprocessing all of said projection measurements, said step of preprocessing further including at least one of gain calibration, reference normalization, logarithmic correction, and beam-hardening correction, said steps of reducing and increasing relative contributions being applied following at least one of said preprocessing steps.

54. The method of claim 43 or 53 wherein said step of constructing includes the steps of filtering and then backprojecting said projection measurements including said projection measurements having reduced and increased contributions.

* * * * *

UNITED STATES PATENT AND TRADEMARK OFFICE
CERTIFICATE OF CORRECTION

PATENT NO. : 4,580,219
DATED : April 1, 1986
INVENTOR(S) : Norbert J. Pelc and Gary H. Glover It is certified that error appears in the above-identified patent and that said Letters Patent is hereby corrected as shown below:

Abstract, line 20, after "method" insert --as disclosed--.

Col. 11, line 26, change "antifacts" to --artifacts--.

Col. 13, line 68, change "$p(\theta,\phi)$" to --$\hat{p}(\theta,\phi)$--.
Col. 15, line 43, change "i" to --is--;
Col. 15, line 54, second occurrence, "$\phi$" should be --$\phi'$--.

Col. 16, line 60, Equation 12, change " $x = \left| \dfrac{\theta-180+2\phi}{\theta_o} \right|$ "

to -- $x = \dfrac{\lfloor \theta-180+2\phi \rfloor}{\theta_o}$ --

Col. 18, line 1 (Eq. 17), "$x^3$" should be --$2x^3$--;
Col. 18, line 65, insert "where" after Equation (22) and before Equation (23).
Col. 24, line 27 through Col. 27, line 9, Claims 42 through 54 should read as follows:

--42. The method of Claim 16 wherein said steps of reducing and increasing relative contributions, and constructing an image are performed without any of the steps of reordering, rebinning and reflecting said projection measurements.--

--43. The method of Claim 42 wherein said steps of reducing and increasing the relative contributions comprises weighting said projection measurements in said first and second predetermined regions with a weighting factor which is a function of the projection angle.--

UNITED STATES PATENT AND TRADEMARK OFFICE
CERTIFICATE OF CORRECTION

PATENT NO. : 4,580,219

DATED : April 1, 1986

Page 2 of 3

INVENTOR(S) : Norbert J. Pelc and Gary H. Glover

It is certified that error appears in the above-identified patent and that said Letters Patent is hereby corrected as shown below:

--44. The method of Claim 43 wherein said weights are selected to be constant for divergent ray measurements within each projection within said first predetermined region.--

--45. The method of Claim 43 wherein said weights are selected to be variable for divergent ray measurements within each projection within said first predetermined region.--

--46. The method of Claim 43 wherein said weighting factors are selected to be lower in said first predetermined region, and higher in said second predetermined regions relative to one another.--

--47. The method of Claim 43 wherein said weighting factors are selected to increase monotonically as functions of time over said first predetermined region at the beginning of said scan.--

--48. The method of Claim 43 wherein said weighting factors are selected to decrease as monotonic functions of time over said first predetermined region at the end of said scan.--

--49. The method of Claim 47 or 48 wherein said weights are selected to be cubic functions of projection angle over portions of said predetermined regions.--

--50. The method of Claim 47 or 48 wherein said weights are selected to be linear functions of projection angle over portions of said predetermined regions.--

--51. The method of Claim 47 or 48 wherein said weights are selected to be piecewise-constant functions of projection angle over portions of said predetermined regions.--

UNITED STATES PATENT AND TRADEMARK OFFICE
CERTIFICATE OF CORRECTION

PATENT NO. : 4,580,219

DATED : April 1, 1986

INVENTOR(S) : Norbert J. Pelc and Gary H. Glover

It is certified that error appears in the above-identified patent and that said Letters Patent is hereby corrected as shown below:

--52. The method of Claim 42 wherein said modality comprises one of transmission-computed tomography and wherein said step of constructing includes the step of preprocessing all of said projection measurements, said step of preprocessing further including at least one of gain calibration, reference normalization, logarithmic correction, and beam-hardening correction, said steps of reducing and increasing relative contributions being applied following at least one of said preprocessing steps.--

--53. The method of Claim 42 or 52 wherein said step of constructing includes the steps of filtering and then backprojecting said projection measurements including said projection measurements having reduced and increased contributions.--

--54. The method of Claim 40 wherein said steps of reducing and increasing relative contributions follow said step of filtering and precede said step of backprojecting.--

Signed and Sealed this

Twentieth Day of January, 1987

*Attest:*

DONALD J. QUIGG

*Attesting Officer*  *Commissioner of Patents and Trademarks*